United States Patent [19]
Baldridge

[11] Patent Number: 5,357,974
[45] Date of Patent: Oct. 25, 1994

[54] BONE MARROW BIOPSY INSTRUMENT

[75] Inventor: Danny J. Baldridge, Greers Ferry, Ark.

[73] Assignees: Thomas F. Robinson; John P. Bethell, both of North Little Rock, Ark.; part interest to each

[21] Appl. No.: 27,062

[22] Filed: Mar. 4, 1993

[51] Int. Cl.$^5$ .............................................. A61B 10/00
[52] U.S. Cl. .................................................. 128/754
[58] Field of Search ........................ 128/749, 751–754; 606/170

[56] References Cited

U.S. PATENT DOCUMENTS

| | | | |
|---|---|---|---|
| 3,175,554 | 3/1965 | Stewart | 128/754 |
| 3,598,108 | 8/1971 | Jamshidi | 128/754 |
| 4,630,616 | 12/1986 | Tretinyak | 128/753 |
| 4,655,226 | 4/1987 | Lee | 128/754 |
| 5,226,426 | 7/1993 | Yoon | 128/753 |

FOREIGN PATENT DOCUMENTS 3644490 7/1988 Fed. Rep. of Germany ...... 128/754

Primary Examiner—Max Hindenburg
Attorney, Agent, or Firm—Stephen D. Carver; Trent C. Keisling

[57] ABSTRACT

A surgical instrument for performing tissue biopsies with a single tissue penetration. The elongated instrument comprises a hollow aspirate needle for aspirating bone marrow fluid, a hollow biopsy needle telescoped within the aspirate needle, and a solid stylet removably telescoped within the biopsy needle, all of which coaxially fit together. The stylet comprises a sharp distal end extending outwardly from the biopsy needle for initially penetrating body tissue and occluding the interior of the biopsy needle. The biopsy needle comprises a distal end normally projecting from the aspirate needle for thereafter penetrating a bone and obtaining a solid bone marrow sample. The bulbous, biopsy needle distal end is sharpened for captivating a specimen. It has a pair of relief slots dividing it into bulbous halves that are compressed together when the needle coaxially moves through the aspirate needle after withdrawal from tissue.

In operation, the instrument is first inserted through skin and muscle tissue to the bone surface. The stylet is then withdrawn. As the instrument subsequently penetrates the cortical bone and enters the bone marrow cavity, the biopsy needle fills with a tissue sample. The biopsy sample is captivated by compression of the bulbous portion as that needle segment is removed. Afterwards, the outer, aspirate needle that remains in place in the bone is suctioned by an attachable syringe, and liquid bone marrow from the marrow cavity is aspirated into the syringe.

18 Claims, 4 Drawing Sheets

U.S. Patent     Oct. 25, 1994     Sheet 1 of 4     5,357,974
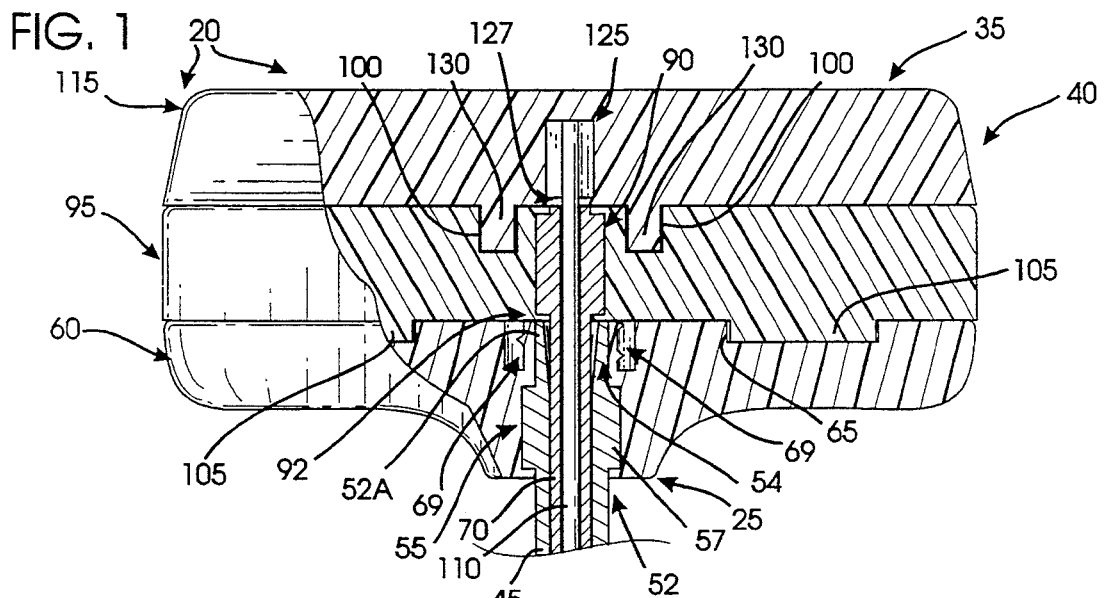
FIG. 1
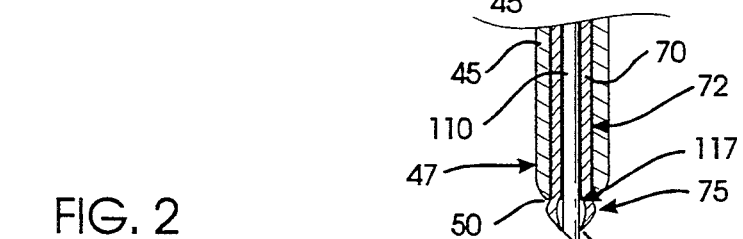
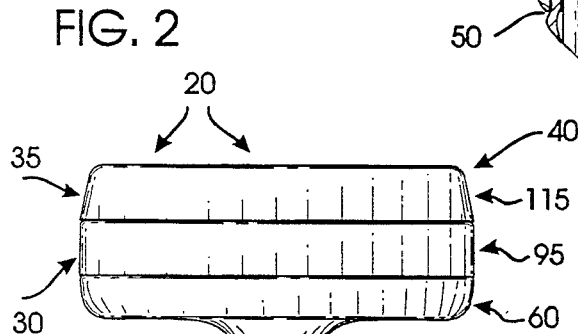
FIG. 2
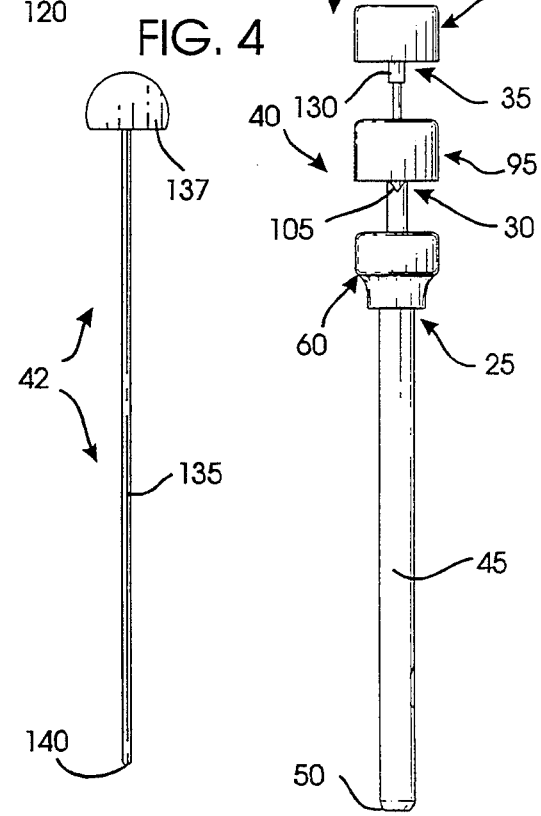
FIG. 3
FIG. 4

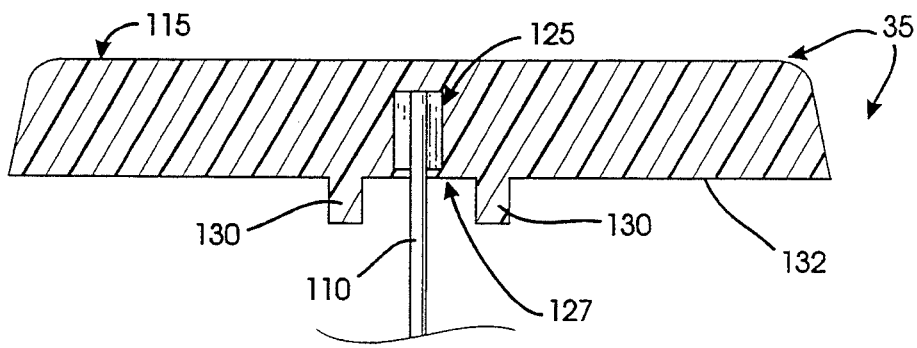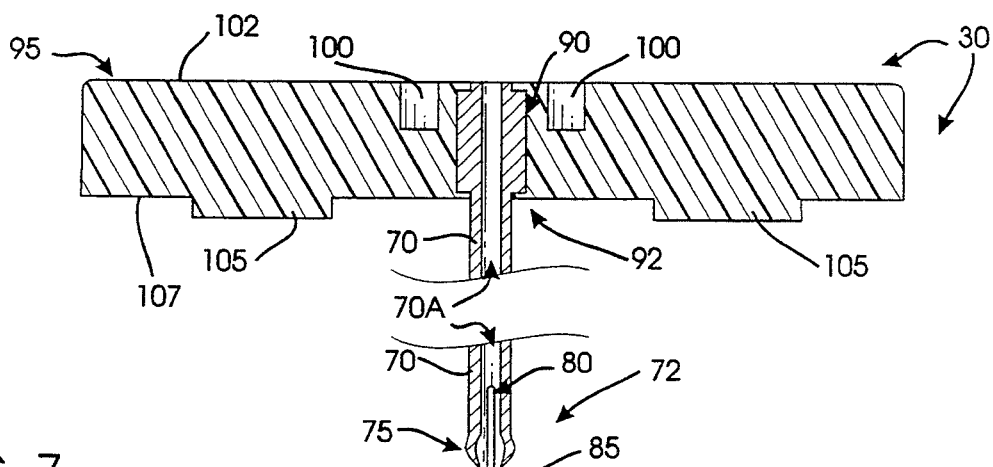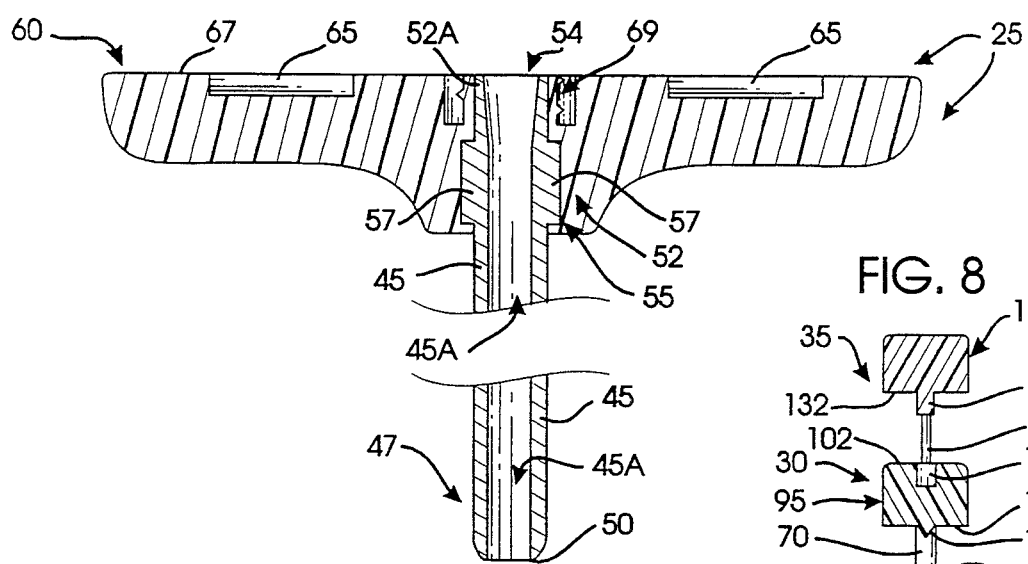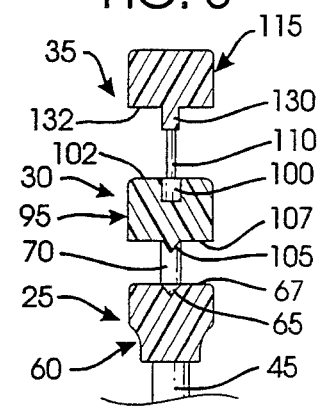

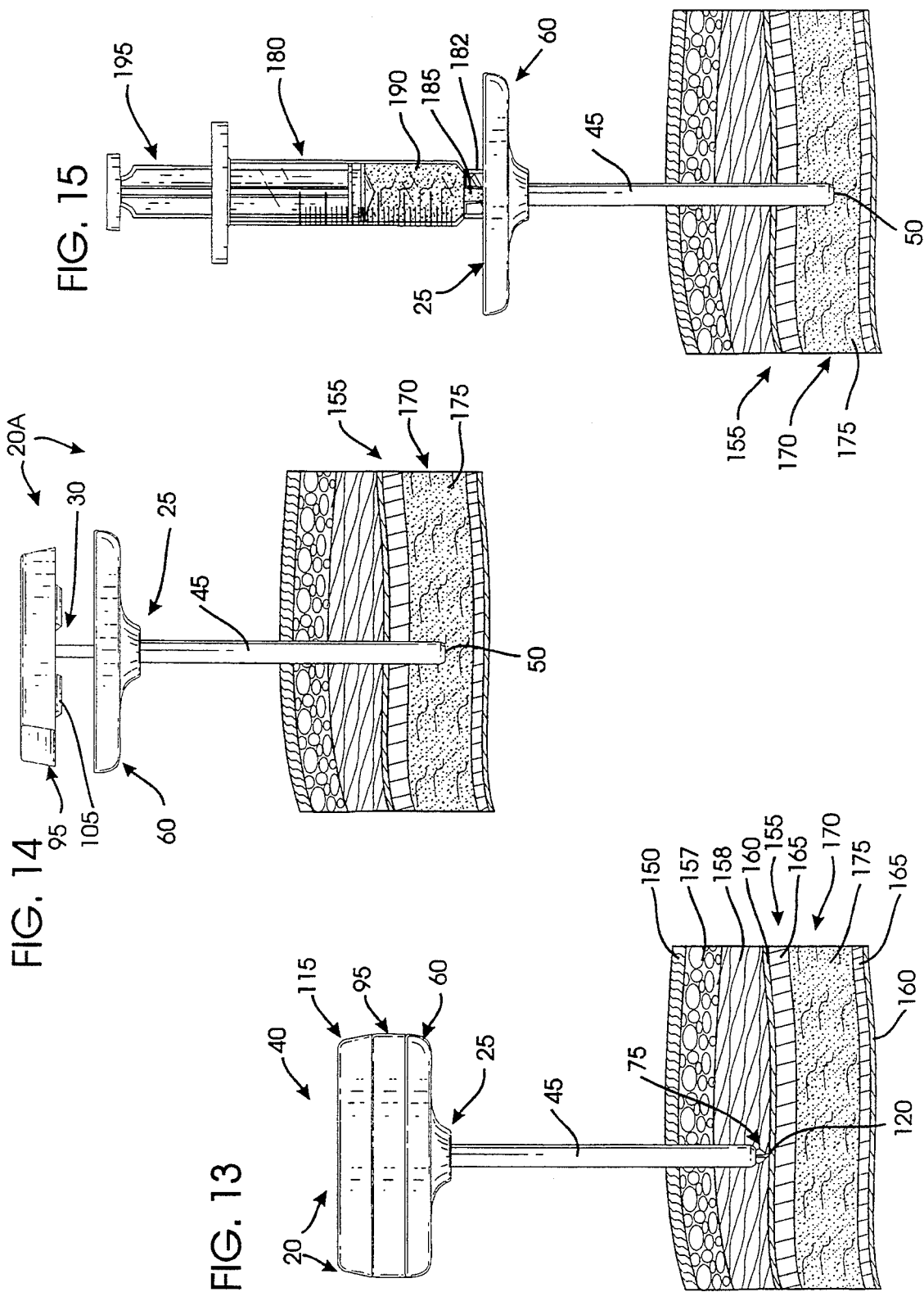

BONE MARROW BIOPSY INSTRUMENT

BACKGROUND OF THE INVENTION

The present invention relates to surgical biopsy instruments. Specifically the present invention relates to bone marrow biopsy instruments and to methods of obtaining specimens of bone, marrow and bone marrow fluid with a single puncture. Art pertinent to the present invention is found in U.S. Patent Class 128, Subclass 754, and to corresponding subclasses within Class 604.

Specimens of bone, marrow and the fluids present in the medullary cavity are biopsied to diagnose various diseases such as cancer and leukemia. It is difficult to obtain these specimens, as human bone has a hard outer cortex encapsulating marrow containing medullary cavity.

Traditionally, marrow biopsies have been taken with large bore needles. A first needle with a bore osculating stylet is inserted through an incision in the patient's skin. It is pressed through the muscle tissue and the cortex of the bone, into the medullary cavity. The stylet is withdrawn and a syringe is attached to the needle. Bone marrow fluid is drawn using negative pressure. The first needle is withdrawn. A second needle is then inserted in a second location into contact with the bone's outer surface, the periosteum. The stylet is removed and considerable force is used to penetrate the cortex of the bone. Once the needle is deep enough into the medullary cavity the needle is shifted to an angular position and gyrated to free the marrow sample for withdrawal.

Aspiration and biopsies are most commonly performed on the hip bone (pelvis) in adults and in long bones such as the femur in adolescents.

Biopsy needles are common in the prior art. U.S. Pat. Nos. 2,991,692; 2,426,535; 2,496,111; 4,272,676; 4,266,555; 4,487,209; and 4,840,184 deal with the overall structure and orientation of the components of biopsy needles.

U.S. Pat. No. 4,469,109 speaks to a more or less conventional aspiration needle which employs the use of a depth stop.

Bone marrow biopsy tips are the subject of several U.S. Patents including Islam, U.S. Pat. No. 4,543,966 and Mehl, U.S. Pat. No. 4,922,602.

The ease of use of a bone marrow biopsy needle will greatly effect the level of trauma visited upon the patient. Therefore, handle design has been addressed by many inventors. U.S. Pat. No. 4,630,616 largely deals with the structure of a handle to facilitate use. U.S. Pat. No. 4,838,282 issued to Strasser Jun. 13, 1989 discloses a needle handle mating surfaces to provide proper alignment of the stylet and needle itself. U.S. Pat. No. 3,893,445 is apparently a fairly early bone marrow biopsy needle having a rather unusual handle configuration which appears to be rather difficult to use.

U.S. Pat. No. 4,258,722 issued to Sessions Mar. 31, 1981 discloses a disposable biopsy needle. It employs a stop and a screwdriver type handle. U.S. Pat. No. 4,655,226 issued to Lee, Apr. 7, 1987, discloses a slightly more conventional biopsy needle also described a being disposable.

The current art includes needle designs that can both aspirate and biopsy the marrow, but they still require two 6 separate procedures and punctures.

The three patents most pertinent to the present invention are Turkel, U.S. Pat. No. 2,496,111; U.S. Pat. No. 3,587,560 issued to Glassman Jun. 28, 1971; and Joishy, U.S. Pat. No. 5,012,818 issued May 7, 1991. Turkel '111 is a soft tissue biopsy needle with a coaxial, dual cannula.

Glassman discloses an inner/outer needle structure intended to sample marrow liquid and bone tissue. A needle is first inserted to aspirate a bone marrow liquid sample. A second needle, with saw teeth, is slid over the first needle and a ring section of bone is cut. Glassman doesn't differentiate between solid marrow and marrow liquid.

Joishy discloses a bone marrow needle that takes a sample with a single puncture. It discloses a bulb shaped handle intended to facilitate use. However, the shaft of the needle has side by side semicircular cannulas resulting in a relatively large outside diameter.

Prior art needles have several drawbacks. The core taken by a biopsy needle often comes out of the needle during withdrawal. The prior does not disclose a coaxial needle small enough in diameter to permit one, as a practical matter, to take a bone marrow biopsy with a single puncture. The single puncture instruments present in the prior art inflict significant trauma on patients in an already weakened physical, mental and emotional state.

Hence, it is desirous to provide a needlelike surgical biopsy instrument to obtain both a solid bone marrow biopsy and liquid bone marrow aspirates using a single entry into the bone. This will result in reduced trauma to the patient. Ideally, this instrument would be easy to use and require a minimal of manipulation once inserted. Specifically if the need to gyrate the needle to free the marrow sample were eliminated much of the pain experienced after the initial insertion of the instrument could be eliminated. Another benefit of a single penetration procedure would be a reduction in the time necessary to take the biopsy. Finally, with only a single insertion the risk of infection would be significantly diminished.

SUMMARY OF THE INVENTION

My invention is a needlelike, surgical biopsy instrument used to obtain both a solid bone marrow biopsy and liquid bone marrow aspirates with a single entry into the bone. Relative to conventional two-puncture procedures, use of the present instrument reduces trauma to the patient. It also lessens the risk of infection and shortens working time.

The instrument consists of two needles and a stylet. The longer, inner needle fits into the shorter outer needle at the proximal end and extends out of the distal end of the outer or aspirate needle. The inner or biopsy needle receives a solid metal stylet which extends out of the distal end of the instrument. Both needles and the stylet are equipped with handles which fit together, one on top of the other.

The aspirate needle comprises an elongated hollow shaft and a base handle. The proximal end of the aspirate shaft defines a ferrule intended to receive the nipple of a syringe. The ferrule has a relatively wide opening tapering to the internal diameter of the remaining shaft. The shaft defines a sharpened distal end. A plurality of ridges extend radially from the shaft near its proximal end. The base handle fits on the proximal end of the aspirate shaft, enveloping the ridges. The base handle defines two "V" shaped groves in its dorsal surface. A recessed, threaded boss is formed around the ferrule to secure the syringe.

The biopsy needle comprises a hollow shaft and a central handle. Radially extending ridges are also defined in the proximal end of the biopsy shaft. A bulbous end with a sharpened edge is formed in the distal end of the shaft. As it is drawn into the shaft of the aspirate needle, diametrically opposed relief slots allow the bulbous end to be compressed. The central handle is disposed generally perpendicularly to the shaft encompassing the ridges. It allows passage of the shaft. The central handle defines two square indentions in its dorsal surface. V-shaped tabs disposed in the ventral surface of the central handle mate with the V-shaped grooves disposed in the dorsal surface of the base handle.

The stylet comprises a solid shaft with a perpendicular cap handle. A sharpened point is defined in the distal end of the stylet shaft. The point extends from the distal end of the assembled instrument to contact and pierce the muscle tissue of the patient. The cap handle encapsulates ridges radially extending from the proximal end of the stylet shaft. Two generally square protrusions extend downwardly from the ventral surface of the cap handle mating with the indentions in the central handle.

In use, after a local anesthetic is administered an incision is made to breach the skin. The instrument is then inserted through the muscle tissue to the periosteum of the patient's pelvis. The stylet is then withdrawn. Downward pressure and short back and forth turns of the remaining needles cause them to penetrate the cortical bone into the bone marrow cavity. This pushes a core of cortical bone and marrow up into the inner biopsy needle.

By placing the stylet back into the biopsy needle, one car judge the size of the biopsy in the needle. The portion of the stylet protruding from the top of the biopsy needle will equal the length of the sample. When the operator feels that an adequate sample is in the biopsy needle, the operator then turns the handle of the biopsy needle (now the top handle) and lifts up on the handle and needle. The biopsy will be locked in the needle due to compression of the bulbous portion. This will compress the tip of the needle, preventing the biopsy from slipping out of the needle as it is removed.

Once the biopsy needle is removed, the outer, aspirate needle remains in place in the bone. The operator attaches a syringe and aspirates liquid bone marrow from the marrow cavity by drawing the syringe's plunger.

Once finished the aspirate needle is removed. Pressure is applied to the puncture, and the patient is bandaged. Thus a solid bone marrow core and liquid bone marrow aspirate have been obtained using a single entry into the bone. Trauma to the patient has been reduced by one half. Risk of infection has also been reduced. Working time has been shortened.

Therefore, a primary object of my Bone Marrow Biopsy Instrument is to provide a single puncture biopsy instrument.

Another fundamental object of my Bone Marrow Biopsy Instrument is to obtain a biopsy of bone, solid marrow and marrow liquid using only a single entry into the bone though overlying tissues.

A related object of the present invention is to reduce trauma to the patient by reducing the number of punctures necessary to take a suitable bone marrow biopsy.

Another object of the present invention is to reduce the risk of infection by reducing the number of intrusions into the patient's body.

Another object of the present invention is to reduce the time necessary to take a bone marrow biopsy.

An object of the present invention is to provide a bone marrow biopsy Instrument which employs a means to free the bone marrow biopsy other than angulation and radial movement of the biopsy needle.

An object of the present invention is to provide a bone marrow biopsy needle with a bulbous end split by relief slots which may be pinched shut as the bulbous end enters a coaxial surrounding shaft thereby captivating a tissue sample.

More specifically, an object of the present invention is to provide a bone marrow biopsy needle that will grasp a bone marrow sample as it is withdrawn from the bone marrow cavity, eliminating the need to tilt the needle to "break" the bone marrow sample free.

An object of the present invention is to provide a bone marrow needle with as small an outside diameter as possible while allowing a solid bone marrow biopsy and bone marrow fluid aspirate to be taken with a single puncture.

An object of the present invention is to provide a bone marrow biopsy instrument with a handle which is of a convenient size and configuration to be used by individuals with smaller hands.

A related object of the present invention is to provide a bone marrow biopsy instrument with a handle that it convenient to use with respect to the forces necessary to perform the procedure for which it is intended.

Another object of the present invention is to provide a bone marrow biopsy Instrument which is coaxial and linear to ease use thereof.

Another object of the present invention is to provide a bone marrow biopsy instrument which allows estimation of the size of the bone biopsy once the instrument is inserted into the patient's medullary cavity.

It is another primary object of the present invention to disclose a method for obtaining a bone marrow biopsy employing only a single intrusion into the patients body and a single puncture of the bone.

Another object of the present invention is to provide a straight-forward, simple to use bone marrow biopsy instrument.

These and other objects and advantages of the present invention, along with features of novelty appurtenant thereto, will appear or become apparent in the course of the following descriptive sections.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIG. 1 is an enlarged partially fragmented front elevational view of my Bone Marrow Biopsy Instrument with portions omitted for clarity and which, like all the below figures, is not drawn to scale;

FIG. 2 is a front elevational view of the assembled instrument;

FIG. 3 is a partially exploded side elevational view of the partially unassembled instrument;

FIG. 4 is an elevation view of the probe employed with the present instrument;

FIG. 5 is an enlarged fragmentary view of the stylet;

FIG. 6 is an enlarged fragmentary view of the biopsy needle;

FIG. 7 is an enlarged fragmentary view of the aspirate needle;

FIG. 8 is a fragmentary longitudinal sectional view of the instrument configured as in FIG. 3;

FIG. 13 is a partially fragmentary environmental view illustrating insertion of the instrument to the periosteum of the bone;

FIG. 14 is a partially fragmentary environmental view of the instrument with the stylet removed, showing the instrument after insertion into the medullary cavity, rotation of the central handle, and partial removal of the biopsy needle; and, FIG. 15 is a partially fragmentary environmental view of the instrument following removal of the biopsy needle, with the instrument mated to a suctioning syringe.

DETAILED DESCRIPTION

Figure 9:
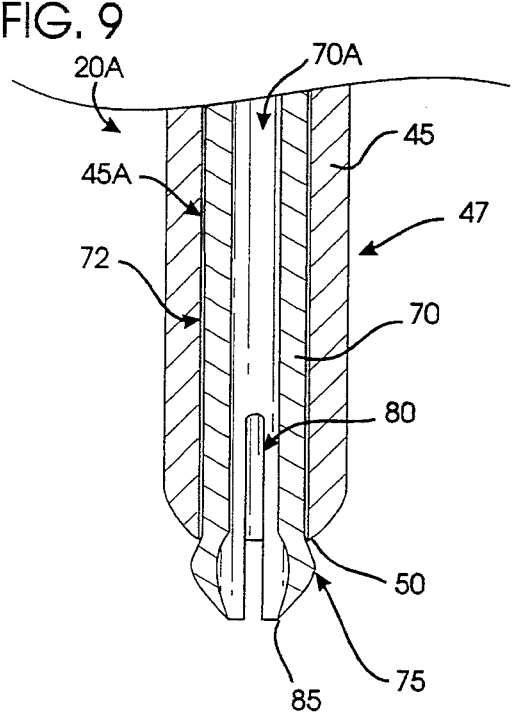
FIG. 9 is a greatly enlarged fragmentary view of the distal end of the present invention with the stylet withdrawn.

Now, with attention directed to the drawings, the herein disclosed Bone Marrow Biopsy Instrument is broadly designated by the reference numeral 20. Instrument 20 is adapted to take a solid bone marrow sample and to aspirate bone marrow fluid with a single puncture of the bone cortex into the medullary cavity. The present bone marrow biopsy instrument comprises an outer hollow aspirate needle 25, a hollow biopsy needle 30 fitted within the aspirate needle 25, and a solid stylet 35 telescoped within the biopsy needle 30. Individual handle portions disposed on the proximal ends of the aforementioned elements form a multiportion instrument handle 40. A separate probe 42 is employed to push a bone marrow biopsy out of the biopsy needle 30.

The aspirate needle 25 is the shortest of the three elements. It is illustrated in detail in FIG. 7. It comprises an elongated hollow shaft 45 and a base handle 60. The shaft 45 defines a bore 45A and terminates at its distal end 47 in a sharpened edge 50 A plurality of ridges 55 extend radially from the aspirate shaft 45 near its proximal end 52. Additionally, the interior of the proximal end 52 of the aspirate shaft 25 defines a ferrule 54. The ferrule 54 is a relatively wide opening at the proximal edge 52A tapering to the internal diameter of the shaft. Ferrule 54 threadably mates with a syringe. The base handle 60 fits on the proximal end 52 of the needle 25 to facilitate use. The base handle 60 in conjunction with the shaft 45 forms a "T" shape. The base handle 60 is preferably constructed of a resilient material such as plastic and molded in place over the ridges 55 defined in the proximal end of the shaft 45. The base handle 60 defines two "V" shaped groves 65 in its dorsal surface 67. A recessed, threaded boss 69 is formed around the ferrule 54 from the material of the handle 60 to retain the syringe.

Preferably, the aspirate shaft 70 has an internal diameter of approximately 3.5 millimeters and an external diameter of approximately 4.0 mm. Thereby giving it a wall thickness of 0.25 mm. The aspirate needle 25 is approximately 10.3 cm long from the distal end 47 to the proximal end 52A. The ridges 55 are approximately 1 mm wide and 1 mm thick. In other words, the extend from the shaft 45 1 mm as well as having a thickness of 1 mm. Preferably, there are four ridges 55; two diametrically opposed long ridges 57 and two diametrically opposed shorter ridges. The long ridges 57 are approximately 8 mm long, while the shorter ridges are approximately 6 mm long.

Figure 10:
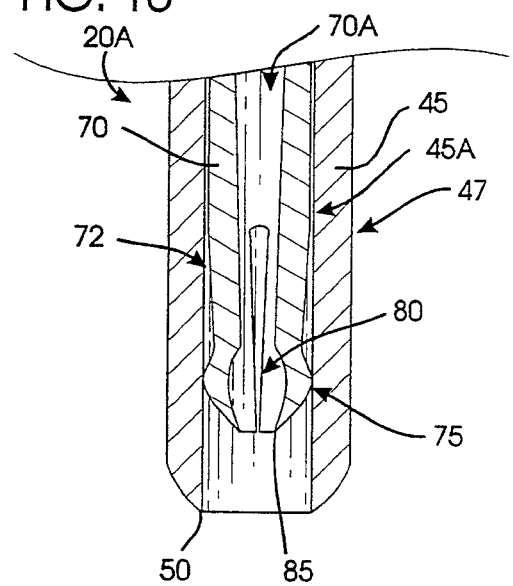
FIG. 10 is a greatly enlarged fragmentary view of the distal end with the biopsy needle partially upwardly withdrawn, illustrating compression of the bulbous end of the biopsy needle.
Figure 11:
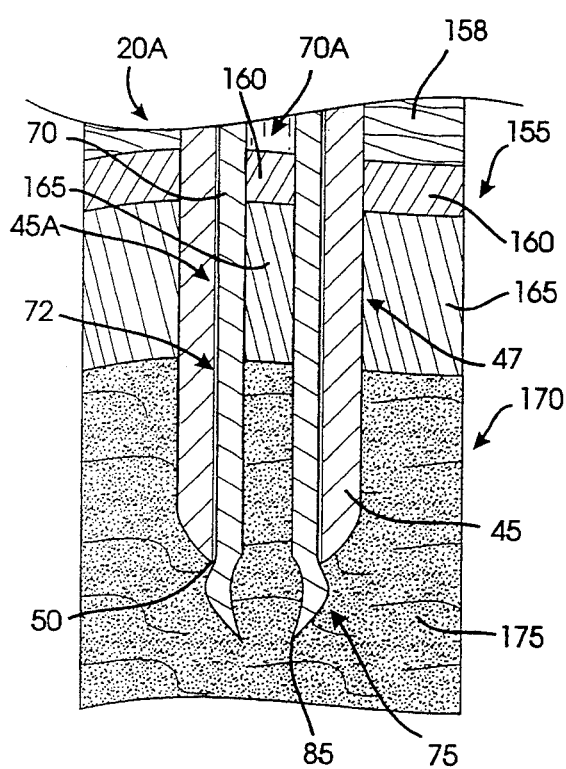
FIG. 11 is a greatly enlarged, fragmentary sectional environmental view of the distal end of the present invention, with the stylet withdrawn, inserted into the medullary cavity.
Figure 12:
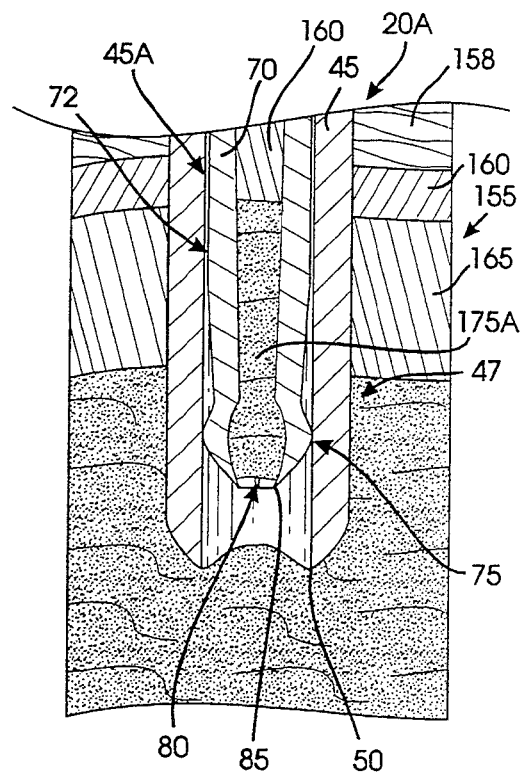
FIG. 12 is a greatly enlarged fragmentary sectional environmental view of the distal end of the present invention, inserted into the medullary cavity, with the biopsy needle partially withdrawn, illustrating compression of the bulbous end to captivate a bone and solid bone marrow sample.

The biopsy needle 30 comprises a hollow shaft 70 defining a bore 70A and a central handle 95. The bore 45A of the aspirate shaft 45 removably receives the biopsy shaft 70. The distal end 72 of the shaft 70 terminates in a bulbous end 75. A pair of diametrically opposed relief slots 80 allow for compression of the distal extreme of the shaft 70 as it is drawn into the shaft 45 of the aspirate needle 25 (FIGS. 9–12). The bulbous end 75 terminates in a sharpened edge 85 defining an inner diameter similar to the internal diameter of the biopsy shaft 70. Ridges 90 extend radially from the proximal end 92 of the biopsy shaft 70. The shaft 70 passes through the generally perpendicular, proximal central handle 95. This central handle 95 is preferably constructed of the same resilient material as the base handle 60. The central handle 95 is formed over the ridges 90 defined in the proximal end 92 of the shaft 70. Two square indentions 100 extend downwardly from the central handle's dorsal surface 102. Tabs 105 defined in the ventral surface 107 have a generally "V" shaped cross section. The tabs 105 mate with the "V" shaped grooves 65 defined in the dorsal surface 67 of the base handle 60 (FIG. 8).

Preferably, the biopsy needle 30 is approximately 11.5 cm in length. The outside diameter of the biopsy shaft 70 is approximately 3.5 mm with a wall thickness of 0.25 mm resulting in an internal diameter of 3.0 mm. The lower 3 mm of the biopsy shaft 70 defines the bulbous portion 75. The bulbous portion is approximately 4 mm wide at its widest, narrowing to a cutting edged opening 85 with an internal diameter of 3 mm to match the internal diameter of the shaft 70. The relief slots 80 are approximately 0.5 mm wide and 7 mm long extending from the distal end 72 toward the proximal end 92 of the shaft 70. Preferably the ridges 90 are approximately 8 mm long and 1 mm wide and thick.

The stylet 35 is a solid shaft 110 with a perpendicular cap handle 115 (FIG. 5). It is slidably disposed in the bore 70A of the biopsy needle shaft 70 occluding the distal end 72. The distal end 117 of the solid shaft 110 terminates in a sharpened angular point 120. This point 120 extends from the distal end of the assembled instrument 20 to contact and pierce the muscle tissue of the patient. Ridges 125 are defined around the proximal end 127 of the shaft 110. The cap handle 115 is formed of the same resilient material as the other handle 40 components. The cap handle 115 encapsulates the ridges 125 defined in the stylet shaft 110. Two generally square protrusions 130 extend downwardly from the ventral surface 132 of the cap handle 115. These protrusions 130 mate with the indentions 100, defined in the dorsal surface 102 of the central handle 95, to index the stylet 35 in place.

The probe 42 comprises a solid flexible shaft 135 and a knob 137 (FIG. 4). The probe shaft 135 is longer than the biopsy needle shaft 70 and has a smaller diameter. It terminates in a blunt end 140.

When assembled the present biopsy instrument 20 comprises the outer aspirate needle 25, with the inner biopsy needle 3 inserted into and extending from the distal end 47 of the aspirate needle 25. The stylet 35 is inserted into the biopsy needle 30. The sharpened end of the stylet 120 extends from the distal end of the biopsy needle 30. The base, central and cap handles 60, 95, 115 fit together to form the instrument handle 40. The handle 40 is rotationally locked together due to the tab and groove structures defined in the various handle components. The V-shaped tabs 105 of the central handle 95 mate with the V-shaped grooves 65 in the base handle 60. The protrusions 130 extending downwardly from the cap handle 115 mate with the indentions 100 in the central handle 95.

METHOD FOR USE OF THE INSTRUMENT

Turning to FIGS. 9 through 15, in an adult the iliac crest or spine of the hip (pelvis) is usually selected for a bone marrow biopsy. Oftentimes in adolescents, a long bone, such as the femur, is used. With the patient lying down and supported on a sturdy surface, such as a table, the assembled biopsy instrument 20 is inserted into an incision in the patient's skin 150 over the bone 155 to be biopsied. Steady pressure is used to push the instrument 20 through the underlying fat 157 and muscle 158 into contact with the periosteum 160, or outer surface, of the bone 155 (FIG. 13). The stylet 35 is then withdrawn from the instrument 20 utilizing the cap handle 115. The remaining two elements of the instrument 20A, the outer aspirate needle 25 and the inner biopsy needle 30, are inserted into the bone 155 by placing firm and steady downward pressure on the central handle 95.

Once the instrument 20 has penetrated the cortical bone 165 a sufficient distance into the bone marrow 175 containing medullary cavity 170. The size of the bone and bone marrow sample 175A held within the biopsy needle 30 is tested using the stylet 35. The stylet 35 is reinserted into the bore 70A of the biopsy needle shaft 70. One can then judge the size of the sample 175A held in the biopsy needle 30 by observing the distance the stylet 35 extends out above the central handle 95. If the sample 175A appears to be of sufficient size, the instrument 20A need not be inserted any further into the medullary cavity 175. The stylet 35 is withdrawn and the central handle 95 is rotated slightly relative to the base handle 60. While the central handle 95 is rotated, it is held in contact with the base handle 60. This allows the "V" shaped tabs 105 extending down from the central handle 95 to "ramp" on the "V" shaped grooves 65 defined in the base handle 60. As the "V" shaped tab 105 ramps upwardly it pulls the biopsy needle 30 upwardly into the bore of the aspirate needle 25. As illustrated in FIGS. 9 through 12, this causes compression of the bulbous portion 75 of the biopsy needle 30 to help captivate the bone marrow sample 175A within the biopsy needle 30. The central handle 95 is employed to withdraw the biopsy needle 30 and the bone marrow biopsy 175A.

The next step, as illustrated in FIG. 15, is screwing a syringe 180 on to the threaded, recessed boss 69 in the base handle 60. A threaded collar 182 is screwed onto the boss 69, mating a central nipple 185 extending from the syringe 180 with the ferrule 54 defined in the proximal end 52 of the aspirate needle shaft 45. A sample of bone marrow fluid 190 is then aspirated by drawing the plunger 195 of the syringe 180. The syringe 180 is then removed and the aspirate needle 25 is removed from the patient. Pressure is applied to the puncture, then bandaged. The bone marrow biopsy 75A is pushed out using the probe 42.

Thus, a solid bone marrow core 175A and liquid bone marrow aspirate 190 have been obtained using a single entry into the bone 155. Relative to conventional two-puncture procedures, trauma to the patient has been reduced. The risk of infection has also been lessened and working time has been shortened.

From the foregoing, it will be seen that this invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A bone marrow biopsy instrument for surgical extracting bone, marrow, fluids and tissue with a single bone puncture, said instrument comprising:

a rigid, elongated, hollow aspirate needle comprising open distal end for aspirating bone marrow fluid;

a rigid, elongated, hollow biopsy needle telescoped within said aspirate needle, said biopsy needle comprising a distal end normally projecting from said aspirate needle distal end for penetrating a bone and obtaining a solid bone marrow sample, said distal end comprising a symmetrical bulbous, sharpened end for captivating a specimen of bone marrow tissue and a set of at least two diametrically opposed longitudinal relief slots defined in said distal end for enabling said bulbous end to compress shut when said biopsy needle is withdrawn from said bone marrow tissue cavity and said bulbous end enters said aspirate needle; and, a rigid, elongated, solid stylet removably telescoped within said biopsy needle, said stylet comprising a sharp distal end extending outwardly from said biopsy needle distal end for initially penetrating body tissue and occluding an interior of said biopsy needle.

2. A bone marrow biopsy instrument as defined in claim 1 wherein:

said aspirate needle comprises a proximal end and a base handle secured to said last mentioned proximal end, said base handle defining at least one V-shaped groove in a dorsal surface of said base handle perpendicular to said aspirate needle; and, said biopsy needle comprises a proximal end and a central handle secured to the biopsy needle proximal end, said central handle comprising V-shaped tabs extending from a ventral surface of said central handle, said tabs normally mating with said grooves;

wherefore, said groove provides a ramp for said tab when said central handle is rotated relative to said base handle while said handles are held in contact, and retraction of said bulbous end into said distal end of said aspirate needle compresses said bulbous end.

3. A bone marrow biopsy instrument as defined in claim 2 wherein said stylet comprises a proximal end and a cap handle secured to said proximal end, said cap handle removably mating with said central handle.

4. A bone marrow biopsy instrument as defined in claim 3 further comprising a plurality of radially spaced apart longitudinal ridges defined in said aspirate needle proximal end, wherein said base handle mates to said ridges.

5. A bone marrow biopsy instrument as defined in claim 4 further comprising a plurality of radially spaced apart longitudinal ridges defined in said biopsy needle proximal end, wherein said central handle mates to said ridges.

6. A bone marrow biopsy instrument as defined in claim 5 further comprising a plurality of radially spaced apart longitudinal ridges defined in said stylet proximal end, wherein said cap handle mates to said ridges.

7. A bone marrow biopsy instrument as defined in claim 6 wherein said aspirate needle proximal end comprises a ferrule and threads for mating with a syringe to withdraw aspirate.

8. A bone marrow biopsy instrument for surgically extracting bone, marrow, fluids and tissue with a single bone puncture, said instrument comprising:

a rigid, elongated, stylet removably telescoped within said instrument for initially penetrating soft body tissue and contacting a bone to be thereafter punctured, said stylet comprising a sharp distal external end extending outwardly from said instrument, a proximal end and a cap handle secured to said stylet proximal end;

a rigid, elongated, hollow biopsy needle for penetrating a bone, after the stylet is removed from the instrument, to obtain a bone marrow sample, said biopsy needle removably telescoped within said instrument and comprising a symmetrical, bulbous sharpened distal end extending from the instrument for puncturing the bone, and a proximal end and a central handle secured to the biopsy needle proximal end, said central handle comprising V-shaped tabs extending from a ventral surface of said central handle, said handle removably mating with said central handle;

a rigid, elongated, aspirate needle comprising an open distal end for entering the punctured bone with said biopsy needle and aspirating bone marrow fluid after said biopsy needle is removed, and a proximal end and a base handle secured to said aspirate needle proximal end, said base handle defining at least one V-shaped groove in a dorsal surface perpendicular to said aspirate needle said grooves normally receiving said tabs; and, wherein said aspirate needle telescopingly receives said biopsy needle and said biopsy needle telescopingly receives said stylet, said groove provides a ramp for said tab when said central handle is rotated relative to said base handle while said handles are held in contact, and retraction of said bulbous end into said distal end of said aspirate needle compresses said bulbous end.

9. The bone marrow biopsy instrument as defined in claim 8 herein said biopsy needle distal end comprises a bulbous sharpened edge and a set of at least two diametrically opposed, longitudinal relief slots, said slots enabling said bulbous end to compress shut and thus captivate a specimen of bone marrow tissue as said biopsy needle is withdrawn and said bulbous end enters said aspirate needle.

10. A bone marrow biopsy instrument as defined in claim 9 wherein said aspirate needle proximal end comprises a ferrule and threads for mating with a syringe to withdraw aspirate.

11. A bone marrow biopsy instrument as defined in claim 10 further comprising a plurality of radially spaced apart longitudinal ridges defined in said aspirate needle proximal end, wherein said base handle mates to said ridges.

12. A bone marrow biopsy instrument as defined in claim 11 further comprising a plurality of radially spaced apart longitudinal ridges defined in said biopsy needle proximal end, wherein said central handle mates to said ridges.

13. A bone marrow biopsy instrument as defined in claim 12 further comprising a plurality of radially spaced apart longitudinal ridges defined in said stylet proximal end, wherein said cap handle mates to said ridges.

14. A bone marrow biopsy instrument for surgically extracting bone, marrow, fluids and tissue with a single bone puncture, said instrument comprising:

a rigid, elongated, hollow aspirate needle comprising an open distal end for aspirating bone marrow fluid;

a base handle secured to a proximal end of said aspirate needle, said base handle comprising V-shaped grooves in a dorsal surface of said base handle, extending perpendicularly relative to said aspirate needle;

a rigid, elongated, hollow biopsy needle telescoped within said aspirate needle, said biopsy needle comprising a distal end normally projecting from said aspirate needle distal end for penetrating a bone and obtaining a solid bone marrow sample, said distal end comprising a symmetrical bulbous, sharpened end for puncturing the bone and captivating a specimen of bone marrow tissue and a set of at least two diametrically opposed longitudinal relief slots defined in said distal end for enabling said bulbous end to compress shut when said biopsy needle is withdrawn from said bone marrow tissue cavity and said bulbous end enters said aspirate needle;

a central handle secured to a proximal end of said biopsy needle, said central handle comprising V-shaped tabs extending from a ventral surface of said central handle, normally mating with said grooves in said base handle, said grooves providing ramps for said tab when said central handle is rotated relative to said base handle while said handles are held in contact, retracting said bulbous end into said distal end of said aspirate needle, compressing said bulbous end;

a rigid, elongated, solid stylet removably telescoped within said biopsy needle, said stylet comprising a sharp, external distal end extending outwardly from said biopsy needle distal end for initially penetrating body tissue, occluding an interior of said biopsy needle and contacting a bone to be thereafter punctured; and, a cap handle secured to a proximal end of said stylet said cap handle removably mating with said central handle.

15. A bone marrow biopsy instrument as defined in claim 14 further comprising a plurality of radially spaced apart longitudinal ridges defined in said aspirate needle proximal end, wherein said base handle mates to said ridges.

16. A bone marrow biopsy instrument as defined in claim 15 further comprising a plurality of radially spaced apart longitudinal ridges defined in said biopsy needle proximal end, wherein said central handle mates to said ridges.

17. A bone marrow biopsy instrument as defined in claim 16 further comprising a plurality of radially spaced apart longitudinal ridges defined in said stylet proximal end, wherein said cap handle mates to said ridges.

18. A bone marrow biopsy instrument as defined in claim 17 wherein said aspirate needle proximal end comprises a ferrule and threads for mating with a syringe to withdraw aspirate.

* * * * *